United States Patent
Wang

Patent Number: 5,867,031
Date of Patent: Feb. 2, 1999

[54] METHOD OF IMPROVING PRESSURE SENSOR MEASUREMENT BY PASSIVE CURRENT COMPENSATION

[75] Inventor: Tak Kui Wang, Havertown, Pa.

[73] Assignee: Hewlett-Packard Co., Palo Alto, Calif.

[21] Appl. No.: 806,367

[22] Filed: Feb. 27, 1997

Related U.S. Application Data

[62] Division of Ser. No. 367,986, Jan. 3, 1995, Pat. No. 5,642, 278.

[51] Int. Cl.$^6$ .............................. G01R 27/08; B01D 15/08
[52] U.S. Cl. .................... 324/721; 364/528.17; 702/133; 95/15
[58] Field of Search ................................. 324/72 D, 721; 364/149, 528.17; 702/114, 130, 133, 138; 95/1, 14, 15, 25; 96/101, 102; 73/861.01, 861.44, 861.52

[56] References Cited

U.S. PATENT DOCUMENTS

| | | | |
|---|---|---|---|
| 4,169,243 | 9/1979 | Payne et al. | 324/720 |
| 4,233,848 | 11/1980 | Sato et al. | 324/721 |
| 4,369,661 | 1/1983 | Gibb | 324/720 |
| 4,994,096 | 2/1991 | Klein et al. | 95/15 |
| 5,108,466 | 4/1992 | Klein et al. | 95/1 |
| 5,193,393 | 3/1993 | Czarnocki | 324/721 |
| 5,214,962 | 6/1993 | Mahrenholz | 324/721 |

*Primary Examiner*—Josie Ballato
*Assistant Examiner*—Diep Do
*Attorney, Agent, or Firm*—Richard F. Schuette

[57] ABSTRACT

A simplified method and apparatus for electronic pressure control with compensation for current operating temperature and pressures in which computer memory is employed for storing a plurality of firmware models which characterize the effects of temperature and pressure variations on (1) fluid flow through the flow restrictor, (2) the temperature sensor, and (3) the pressure sensor, so that control signals can be generated which compensate a plurality of thermally coupled sensors for changes in current operating temperatures and pressures.

6 Claims, 9 Drawing Sheets

METHOD OF IMPROVING PRESSURE SENSOR MEASUREMENT BY PASSIVE CURRENT COMPENSATION

CROSS REFERENCE TO RELATED APPLICATION(S)

This is a divisional of application Ser. No. 08/367,986 filed on Jan. 3, 1995 now U.S. Pat. No. 5,642,278.

FIELD OF THE INVENTION

The present invention relates to methods and apparatus for providing distribution and regulation of fluids and, more particularly, to a temperature compensated pneumatic manifold for accurate control of fluid pressure and flow.

BACKGROUND OF THE INVENTION

It is well known that fluid flow may be regulated electronically by employing an electronically controlled fluid regulator for adjusting the pressure of the fluid upstream of a flow restrictor in response to a control signal generated by a pressure sensor positioned upstream of the flow restictor. In the automotive field, such fluid regulation might be employed in the intake manifold or fluid distribution system of a gasoline engine. In the field of gas chromatography, the gas chromatograph (GC) detectors require accurately regulated fluid supplies, the distribution of which is performed by a pneumatic manifold.

A gas chromatographic apparatus, well known in the prior art, is shown in FIG. 1. The chromatograph 10 is arranged in a forward pressure regulated design suitable for direct injection. The detector 30 can be any of the GC detectors known in the art Typically, the detector 30 determines the magnitude of the physicochemical property over time. The performance of many chromatographic detectors is dependent upon the flow rate or pressure of the support fluid employed. By modifying the pressure or flow rate of the detector support fluids, one can for example, optimize detector sensitivity in an flame photometric detector (FPD) or flame ionization detector (FID), or to minimize solvent quenching of an nitrogen phosphorous detector (NPD) bead.

As well known in the prior art, and as illustrated in FIG. 1, a typical detector pneumatic manifold supplies three fluid sources 13a, 13b, 13c to three separate valves 14a, 14b, 14c. The valves serve to control both the pressure and the flow rate of the support fluid components. Flow through flow restrictors 15a, 15b, 15c provide back pressure such that sensors 16a, 16b, 16c can generate stable electronic signals in relation to the pressures or the flow rates of the component fluids. Pressure signals are provided to a processor 40, which in turn provides control signals to the valves 14a, 14b, 14c to regulate the pressure of the component fluids.

The processor 40 can maintain the pressure at some desired level by generating control signals directing the operation of the valves 14a–c. Since the generated control signals are in a digital form, they are converted to analog form by a digital to analog converter and appropriately amplified by an amplifier prior to transmission to valves 14a–c. The fluid pressures as sensed by the sensors 16a–c are provided to the processor 40 by first converting the analog signals generated by the pressure sensors 16a–c from an analog to digital signal by an A/D converter. The digital signals generated by the converter are supplied to the processor 40.

Unfortunately, the flow rate of a fluid through the flow restrictors 15a–c is unstable and varies with flow restrictor construction, the type of fluid flowing through the flow restrictor, the temperature of the fluid (essentially the manifold temperature) and the pressure of the fluid both upstream and downstream from the flow restrictor. Additionally, the pressure sensors 16a–c are sensitive to variations in temperature which can lead to errors in flow regulation. There exists a need for more stable detector fluid flows and reduced manifold temperature variations to provide better chromatographic area repeatability.

One method for eliminating temperature sensitivity is to enclose the flow sensing and controlling devices in a controlled heated zone constructed with thermally insulating material. Temperature sensors and heaters inside the heated zone provide feedback to maintain the flow restrictor and pressure sensor temperatures constant and thereby remove temperature as an error-producing variable.

Unfortunately, the incorporation of a heated zone increases manufacturing costs related to instrument calibration and components. Additionally, instrument reliability is reduced as the components required to regulate a heated zone are more likely to fail with continual operation at manifold temperatures higher than ambient. Furthermore, a heated zone requires a long start-up time to stabilize prior to instrument operation.

Another technique for correcting the inaccuracy of the pressure flow relationship due to flow restrictor variation and temperature dependencies is to perform extensive, multi-point calibrations at a very large number of different operating temperatures and pressures. The results of such calibrations are saved in an EEPROM and employed for adjusting the feedback signal to the control valve. The calibration points relate pressure sensor signals outputs, ambient pressure signal outputs, and a temperature signal to fluid flow rate through the flow restrictor. A separate set of calibrations is required for each fluid and flow restrictor combination. Unfortunately, the cost of such calibrations make this technique commercially unreasonable.

A need exists for a pneumatic manifold design which automatically compensates fluid flows for ambient temperature and pressure changes without the use of a heated zone.

SUMMARY OF THE INVENTION

The present invention provides a simplified method and apparatus for electronic pressure control with ambient temperature and pressure compensation of detector fluid pressure and flow. A pneumatic manifold includes a plurality of thermally coupled sensors which measure and generate signals related to fluid pressure at both the high pressure side and low pressure side of a flow restrictor, as well as the temperature of the flow restrictor and the pressure sensors.

Computer memory is employed for storing a plurality of firmware models which characterize the effects of temperature and pressure variations on (1) fluid flow through the flow restrictor, (2) the temperature sensor, and (3) the pressure sensor. For example, fluid flow through the flow restrictor may be characterized as:

$$Q = [\alpha f]* \frac{(P_s + P_a)^2 - P_a^2}{T_f^a} + [\beta f]* \frac{P_s}{T_f^5}$$

In order to determine the unknown constants, the pneumatic manifold is operated in a pneumatic manifold carrier at a plurality of known temperatures and pressures such that a plurality of sensor output voltages can be measured. The constants $\alpha f$ and $\beta f$ from the flow equations are obtained by substituting the measured sensor output voltages into the Flow Restrictor Equation and solving for the constants.

Current operating temperatures and pressures are measured and inputted into the characterizing equations in order to generate the drift output voltages for modifying the output voltages of the plurality of sensors to compensate for the variations in operating temperatures and pressure.

Alternatively, a look-up table may be created prior to operation of the pneumatic manifold by inserting a range of ambient temperatures and pressures into the Flow Restrictor Equation. During operation, ambient temperature and pressure are measured and employed for accessing the corresponding drift voltage from the look-up table. Modified sensor output voltages are obtained by combining the sensor output voltages with the plurality of drift voltages. These steps are repeated continuously throughout operation of the pneumatic manifold to ensure real-time compensation for ambient temperature and pressure changes.

In order to control fluid flow through the flow restrictor, the modified pressure sensor output voltage is employed as a feedback control signal for opening and closing a proportional valve between the source of fluid and the flow restrictor.

The flow restrictor, pressure and temperature sensors may be thermally coupled to minimize errors caused by temperature variations and to simplify the firmware model.

Other aspects and advantages of the present invention will become apparent from the following detailed description, taken in conjunction with the accompanying drawings, illustrating by way of example the principles of the invention.

DETAILED DESCRIPTION OF THE PREFERRED EMBODIMENTS

Figure 1:
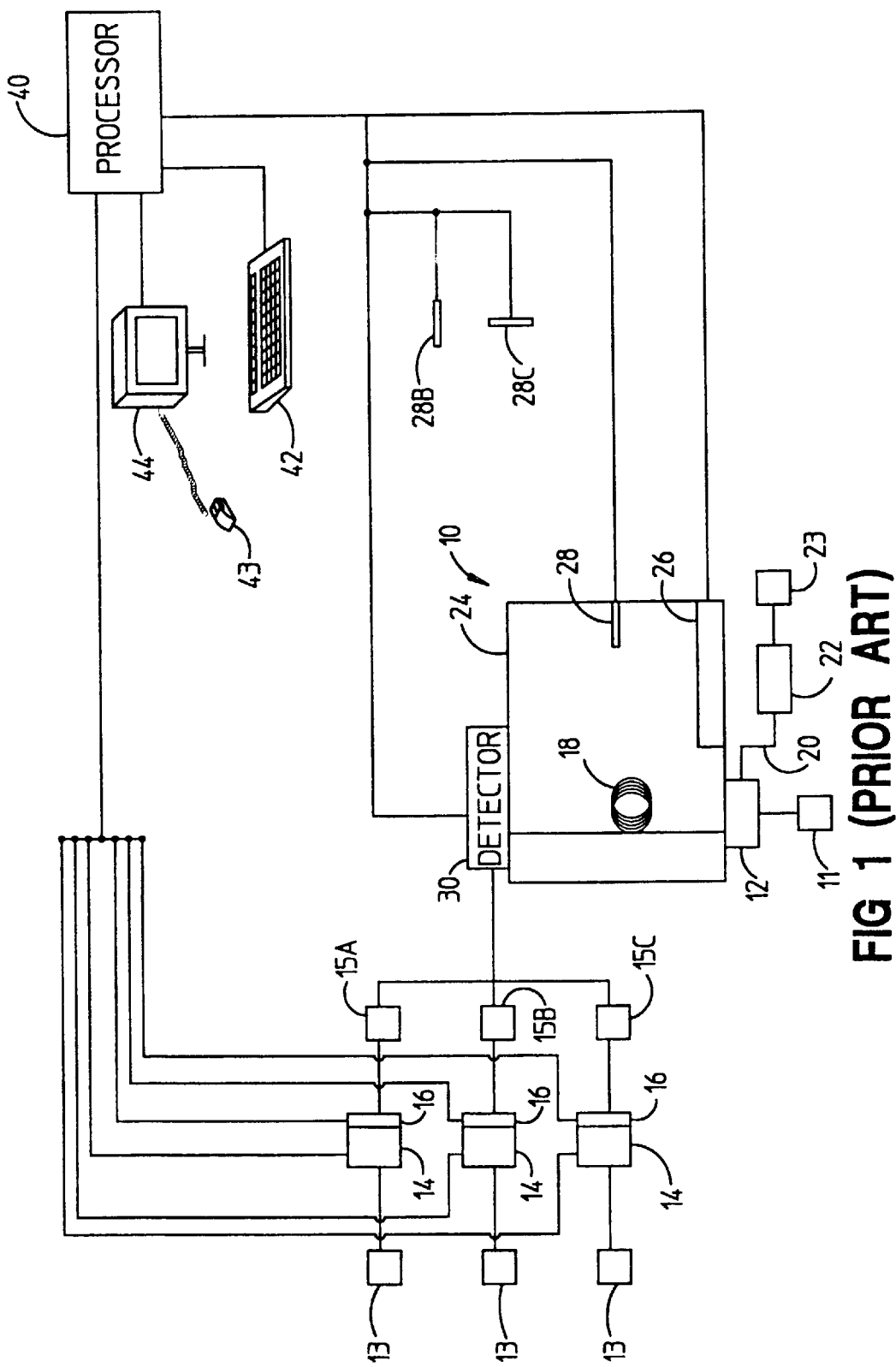
FIG. 1 is a simplified schematic representation of a prior art gas chromatograph having three detectors with electronically controlled support fluids.
Figure 2:
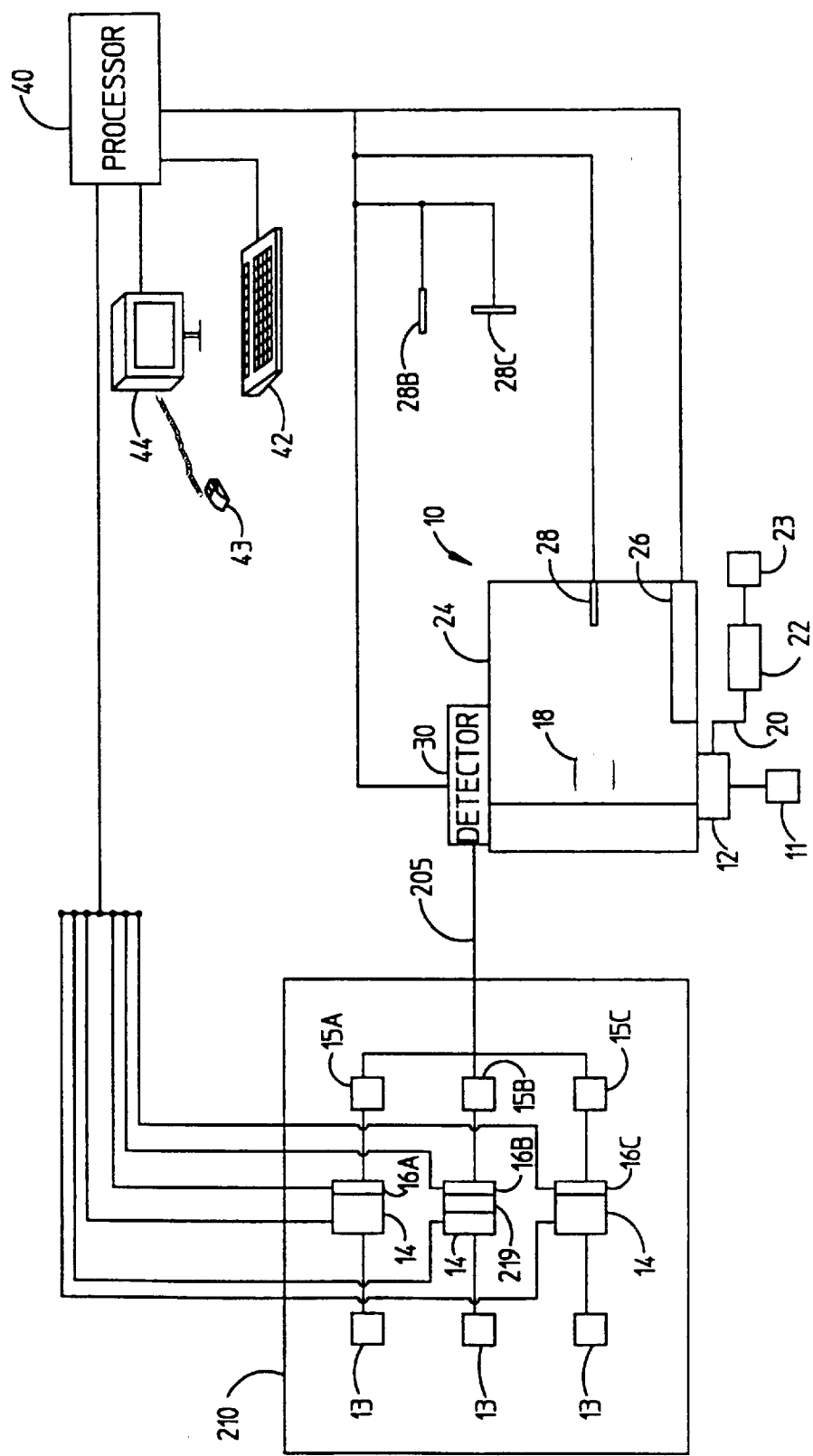
FIG. 2 is a simplified schematic representation a gas chromatograph having three detectors with electronically controlled support fluids in accordance with the preferred embodiment of the invention.

FIG. 2 illustrates a preferred embodiment of the invention as embodied in a gas chromatograph 10 having electronic pressure control with ambient temperature and pressure compensation of the pressure and flow of detector support fluids 205. A detector pneumatic manifold 210 typically supplies three fluid sources 13a, 13b, 13c to three separate valves 14a, 14b, 14c. The valves serve to control the pressure and the resulting flow rate of the support fluid through the flow restrictors 15a, 15b, 15c. The pressure sensors 16a, 16b, 16c provide stable output voltage levels in relation to the pressure of their corresponding support fluids. A temperature sensor 219 is coupled to pressure sensor 16b. All of the pressure sensors 16a, 16b, 16c and the flow restrictor are mounted on a thermally conductive bar such that the output voltage of the temperature sensor 219 represents the temperature of all of the pressure sensors and the flow sensor.

Figure 3:
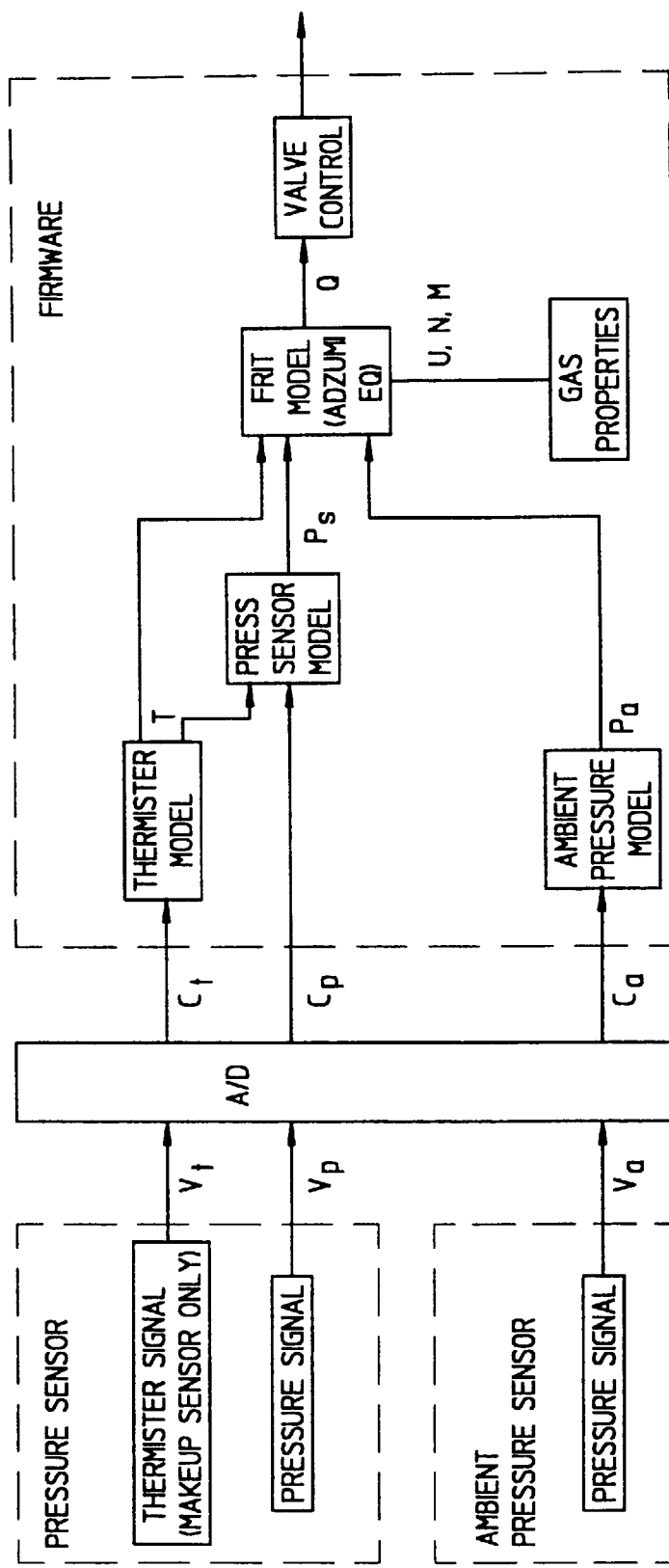
FIG. 3 is a block diagram depicting the relationship between the firmware models.

In order to provide compensation, a plurality of drift voltages are calculated by inputting current temperature and pressure values into four firmware models which characterize the effects of ambient pressure and temperature changes on fluid flow restrictor, effects of temperature on pressure sensor and temperature sensor output. Once calculated, the drift voltages are added to the sensors 16a–c output voltages to ensure proper control of the corresponding proportional valve. The relationship between these numerical models is illustrated in FIG. 3. A detector typically has one or more support fluids, each of which will require one or more numerical models to provide adequate compensation.

II. Derivation of Flow Restrictor, Temperature Sensor and Pressure Sensor Model 1. Flow Restrictor Model The Flow restrictor model is based on the work of A. E. Scheidegger entitled "The Physics of Flow Through a Porous Media", University of Toronto Press, Toronto 1974, PP 172, in which:

$$v = \frac{\pi \cdot E \cdot dpr}{8 \cdot A \cdot ug} + e \cdot \left(\frac{4}{3}\right) \cdot \sqrt{2 \cdot \pi} \cdot \sqrt{\frac{R \cdot Tg}{M}} \cdot \frac{F}{A \cdot pr} \cdot dpr$$

where:

v="Seepage velocity"

e=Adzumi constant=0.9

A=Cross-sectional area of the porous media $$E = \frac{N \cdot r^4}{t} \quad N = \text{number of pores in area } A$$

$$r = \text{average radius of pores}$$

$$F = \frac{N \cdot r^3}{t} \quad t = \text{thickness of porous media}$$

R=universal gas constant

M=Molecular weight of the gas ug=Gas viscosity pr=Gas pressure dpr=Delta pr

Tg=Gas temperature

This equation can be modified to model fluid flow through a flow restrictor to provide:

$$Q = \frac{[\alpha]}{U \cdot T_f^{N+1}} \cdot (P_s^2 + P_a^2) + \frac{[\beta]}{(M \cdot T_f)^5} \cdot (P_s - P_a)$$

Where:

Q=gas flow (sccm)

$P_s$=source pressure (psia)=[gage pressure]+[atmos pressure]

$P_a$=downstream pressure (psia)=[normally atoms pressure]

$T_f$=temperature of frit (degK)=degC]+273.18

U,N=viscosity constants which depend on the gas (viscosity in micropoises)

M=molecular weight of gas alpha=constant which is a property of the restrictor and is determined through calibration beta=constant which is a proerty of the restrictor and is determinbed thorugh calibration The equation can be modified for use by firmware to provide:

$$Q = [\alpha f]* \frac{(P_s + P_a)^2 - P_a^2}{T_f^n} + [\beta f]* \frac{P_s}{T_f^5}$$

where: $p_1$=source gauge pressure (psig)=$P_s$−[atmos pressure]

$\alpha f=[\alpha]/U$ $\beta f=[\beta]/(M^{0.5})$ n=N+1

The constants "$\alpha f$" and "$\beta f$", are determined by running each manifold through a calibration procedure at two known flow rates such that the output voltages corresponding to the flow rates can be substituted into the flow equation for determining the constants. Once the constants have been determined for each flow restrictor (and for each type of fluid flowing through the flow restrictor), they are substituted back into the models and the complete models are stored for retrieval during system operation. In the preferred embodiment, atmospheric pressure is used to approximate the pressure downstream from the flow restrictor. Thus, an error term will be introduced to the extent that there is a pressure drop downstream of the flow restrictor. In an alternative embodiment, a downstream pressure sensor may be included to provide actual downstream pressure into the flow restrictor model for more accurate compensation of downstream ressure drops.

2. Temperature Sensor Model

The temperature of the flow restrictor effects fluid flow through the flow restrictor. A temperature sensor model is developed which characterizes the response relationship between flow resticltor temperature and the output of a temperature sensor mounted in thermal contact with the flow restrictor. A linear approximation of this response relationship necessitates only two calibration points, in particular:

$$C_t=E+F*t_c$$

where: $C_t$=thermistor response (A/D counts)

E=offset at 0 degC (A/D counts), F=temperature sensitivity (A/D counts per degC) and $t_c$=calibration temperature.

3. Upstream Pressure Sensor Model

A model of the response relationship between the upstream pressure sensor and the pressure source and the temperature of the pressure sensor may be characterized as:

$$C_p=A+C*t_c+(B+D*t_c)*p_1$$

where: $C_p$=sensor response (A/D counts)

A=offset at 0 degC and 0 psig (A/D counts)

B=pressure sensitivity (counts/psi)

$p_1$=source gauge pressure (psig)=$P_s$−[atmos pressure]

$t_c$=thermistor temperature (deg C.)

The first derivative of the pressure sensor equation ($dC_p/dt_c$) is a function of pressure and characterizes the drift of the pressure sensor output signal (or temperature sensitivity), in particular:

$$dC_p/dt_c=C+D*p_1$$

Where:

C=temperature sensitivity (A/D counts per degC)

D=pressure sensitivity change with temperature (A/D counts per psi per deg C.)

Combining equations are rearranging: The constants A, B, C, & D are determined by calibration in the manner set forth below.

III. Calibration Procedure

Figure 4:
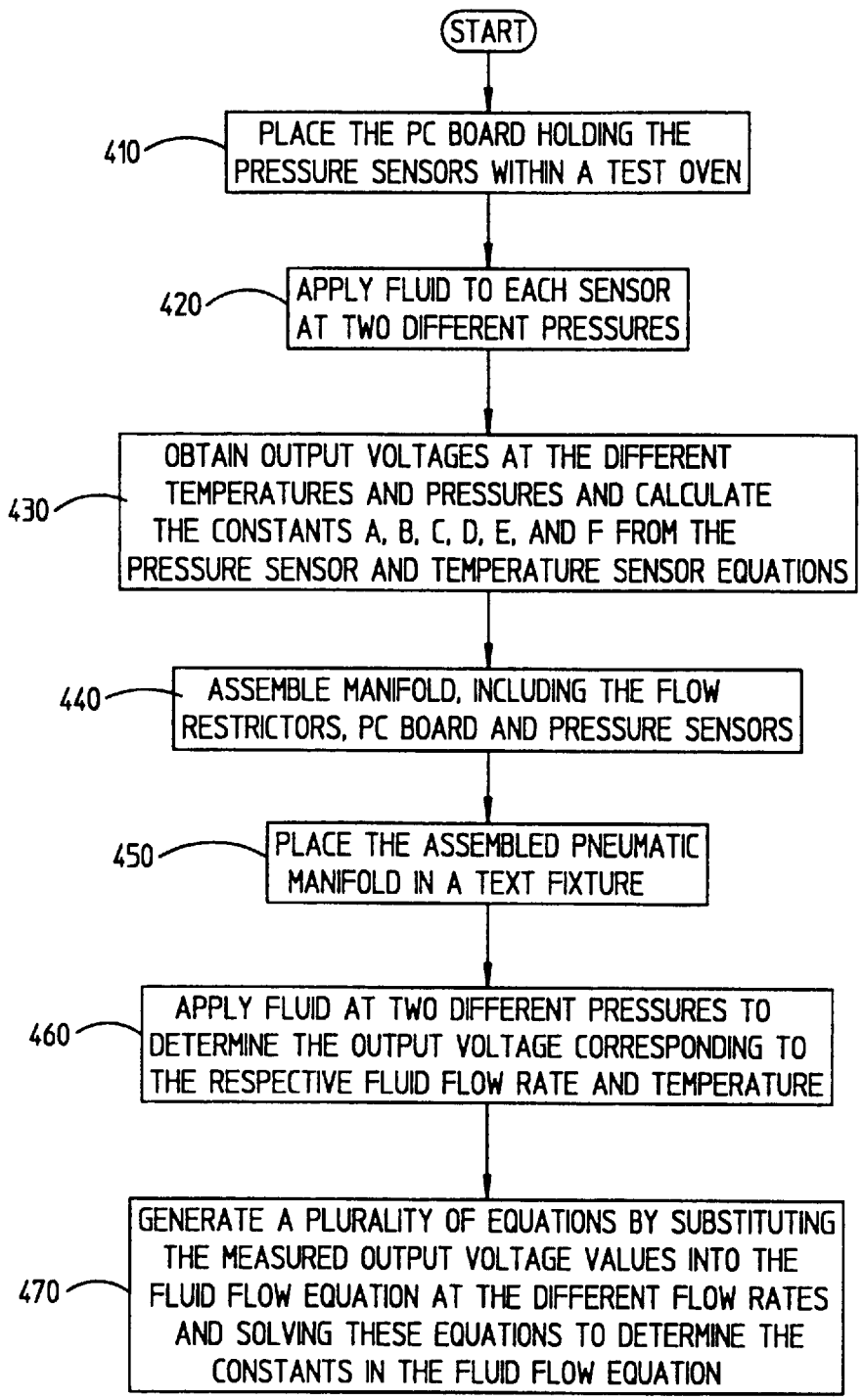
FIG. 4 is a flow chart illustrating the calibration procedure.
Figure 5A:
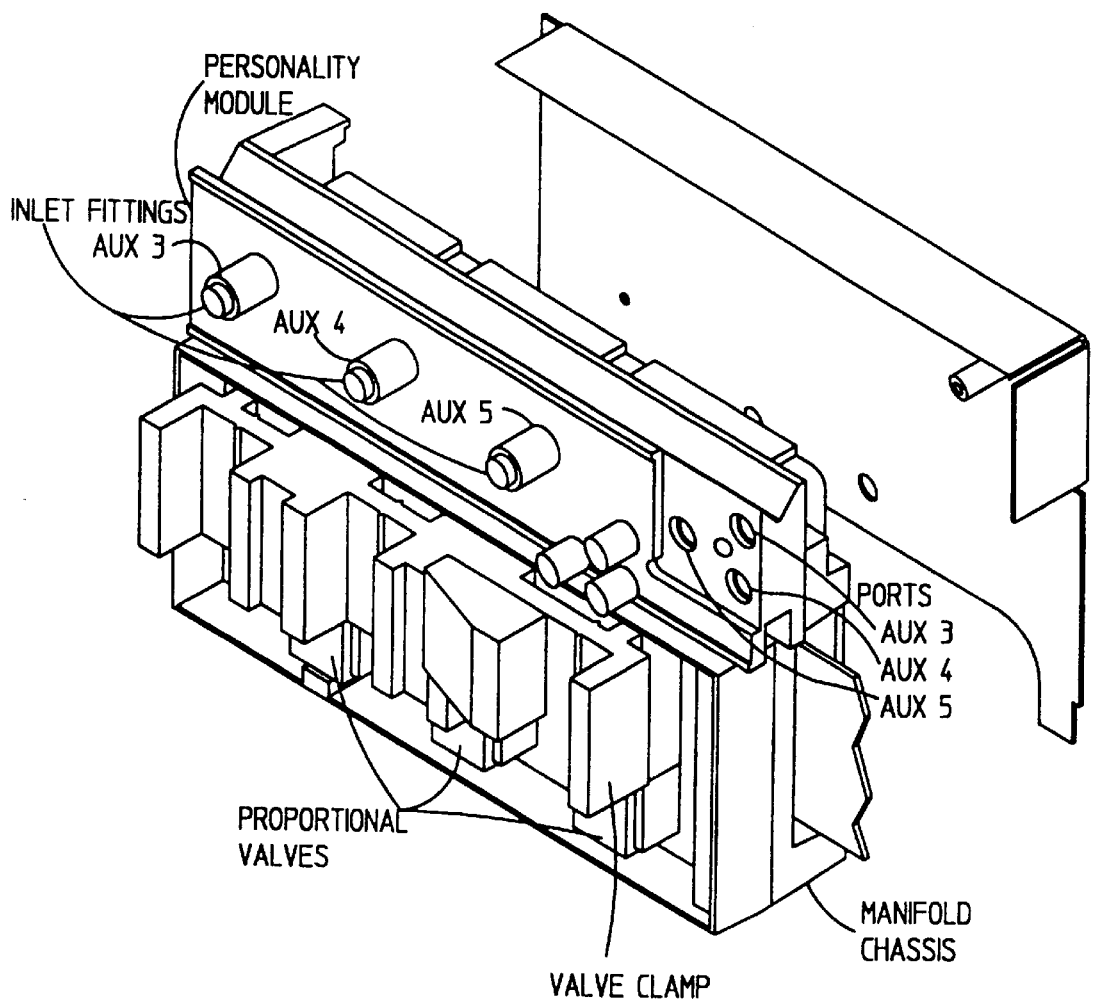
FIG. 5A is a perspective view a front side view of a detector manifold.
Figure 5B:
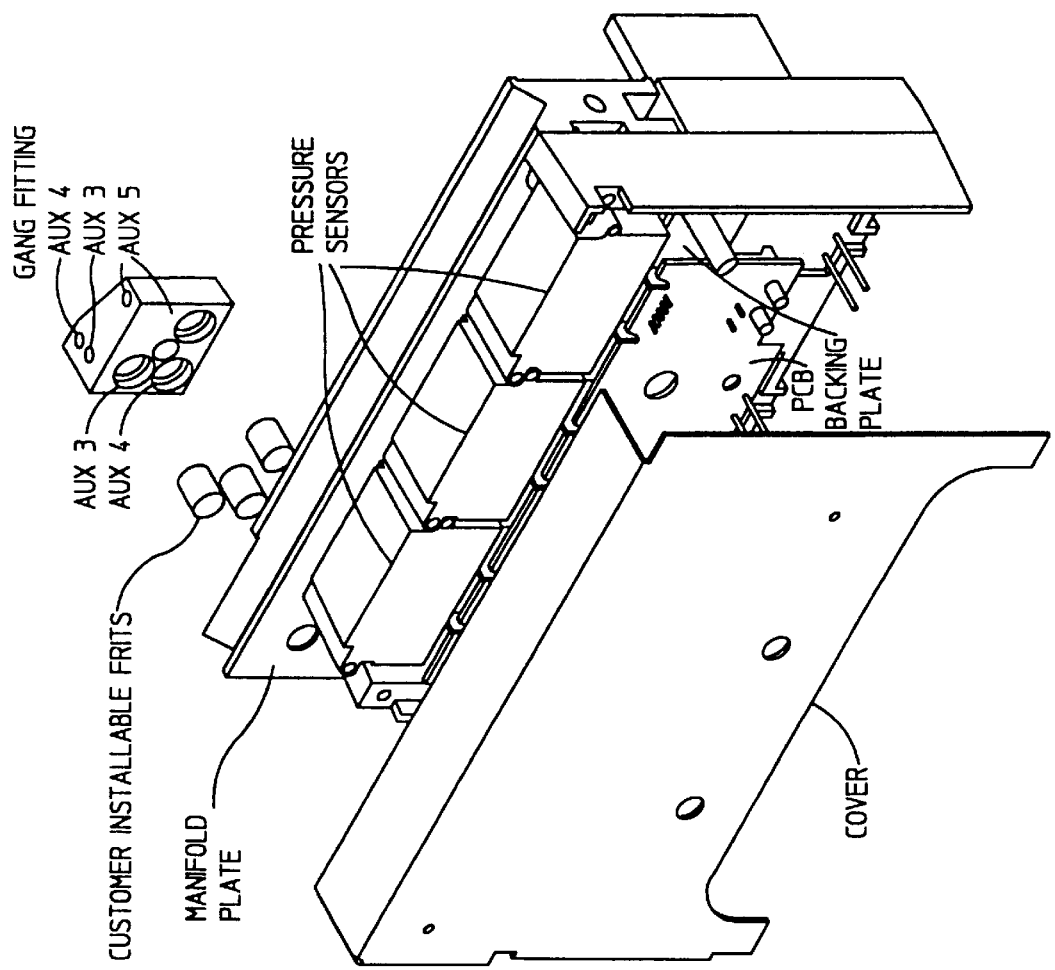
FIG. 5B is a perspective view of a back side view of a detector manifold.

FIG. 4 is a flow chart illustrating the steps in the calibration procedure. At step 410, a PC board holding the pressure sensors is placed within a test oven; at step 420, fluid is applied to each sensor at two different pressures; at step 430 the output voltages obtained at the different temperatures and pressures are employed for calculating the constants A, B, C, D, E and F from the Pressure sensor and Temperature sensor equations; at step 440, the manifold is assembled and includes the flow restrictors, PC board and pressure sensors; at step 450, the assembled pneumatic manifold is placed in a text fixture; at step 460, fluid is applied at two different pressures and the output voltage corresponding to the respective fluid flow rate and temperature; and at step 470, a plurality of equations are generated by substituting in the measured output voltage values into the fluid flow equation at the different flow rates, these equations are solved simultaneously to determine the constants in the fluid flow equation.

The firmware models include unknown constants which must be determined for each type of detector support fluid.

In particular, for each pressure sensor, the pressure sensor output voltage Vo is measured (relating pressure to A/D counts) at two pressures (one of which can be 0 psig), each of which are conducted at two different temperatures representing the anticipated GC temperature operating range (one temperature nominally 35 deg). For each flow restrictor, pressure sensor output voltages Vo data is obtained to characterize fluid flow versus pressure at two flow rates other than zero flow and at a nominal 35 deg C. Such data is required for each fluid used in the channel. For the Thermistor Model, data must be gathered which characterizes temperature sensor temperature vs A/D converter counts at two different temperatures.

In an alternative embodiment of the invention, the flow restrictor and the pressure sensor each include a temperature sensor such that they do not have to be thermally coupled. The firmware model must be modified accordingly. Additionally, a pressure sensor could be added to the downstream side of the flow restrictor to replace the ambient pressure measurement.

IV. Electronics

Figure 6:
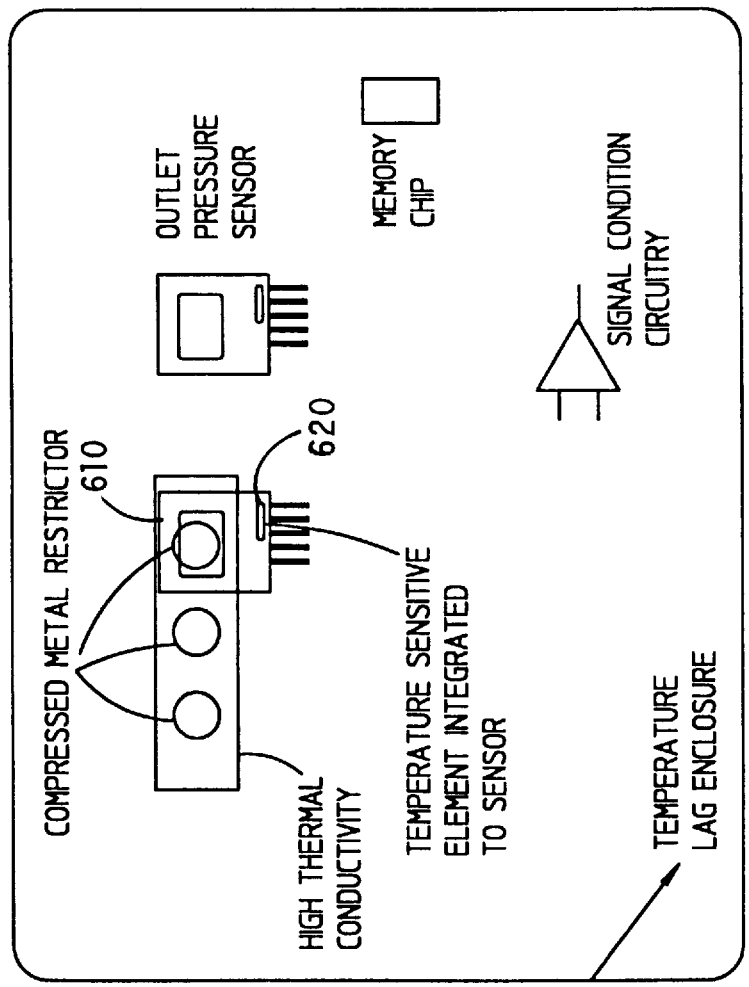
FIG. 6 is a illustration of several flow restrictor's coupled thermally by a high thermal conductive bar.

FIG. 6 illustrates a typical configuration of the hardware portion of the invention. Several flow restrictors are shown coupled thermally to each other through a high thermal conductive bar. Aluminum is the construction material. Only one pressure sensor is shown mounted on the unit, which measures the upstream pressure of a flow restrictor. The pressure sensor is mounted to provide intimate thermal contact with the conductive bar. In the preferred embodiment, low pressure side of all the flow restrictors are vented to the ambient. A single ambient pressure sensor is employed and the measured pressure signal is used for all measurements. When the low pressure side of the restrictors are not at the same pressure multiple pressure sensors may be required.

In summary, the steps employed for generating a characteristic equation include:

Measure flow at two temperature and pressure to calculate α, β and tempco; Linearize for small flow and pressure range; measure da/dT and db/dT for temperature compensation, and calculate da/dT and db/dT from characteristic flow equation.

Figure 7:
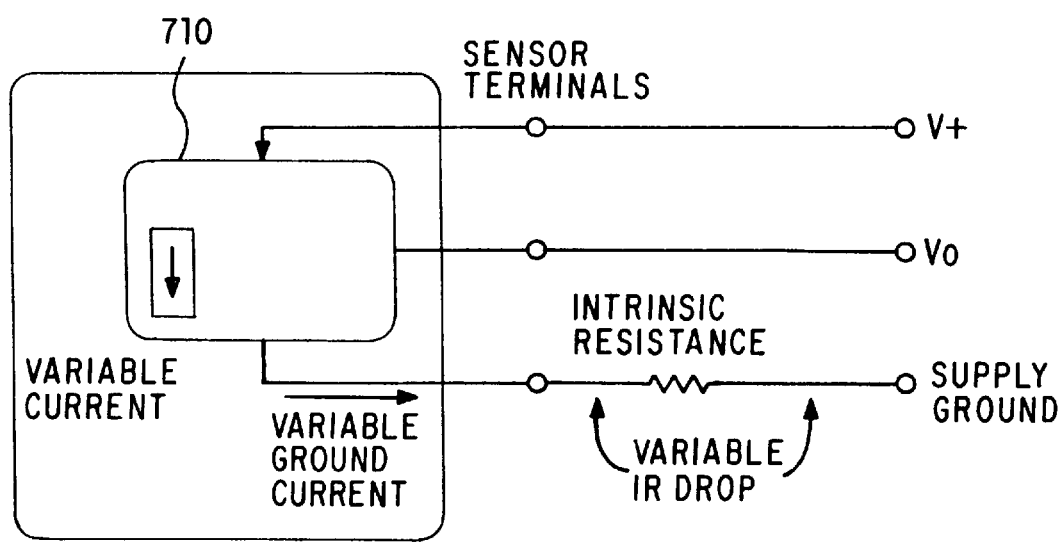
FIG. 7 is a schematic diagram of a prior art pressure sensor with variable return current.

FIG. 7 shows the schematic drawing of a pressure sensor which generates a variable current during operation and returns to ground as a variable return current. The intrinsic resistance shown in FIG. 7 represents the total resistance from the ground terminal of the sensor to the reference ground of the power source. A voltage drop equal to product of the ground current of the sensor and this intrinsic resistance. The voltage drop, due to this return current and any intrinsic resistance should not be taken lightly. In a typical sensor application, the bandwidth of the sensor is direclty related to the current. On the other hand, with increasing circuit density due to surface mount, conductor width on printed circuit boards decreases. Typical trace width of 0.008" on a 0.5 oz copper printed circuit board contribute resistance of 60 milli ohm per inch. Connector resistance can also vary by tens of milliohms. The voltage drop can seriously affect signal integrity at micro volt and even milli-volt level. While current loops are insensitive to conductor resistance and are used extensively for remote signal transmission, the bandwidth is only limited. Active ground circuitry are also used extensively, they sometimes posed stability problem. High bandwidth design is also required to achieve good forced ground. They will not eliminate voltage drop across the sensor connector either.

Figure 8:
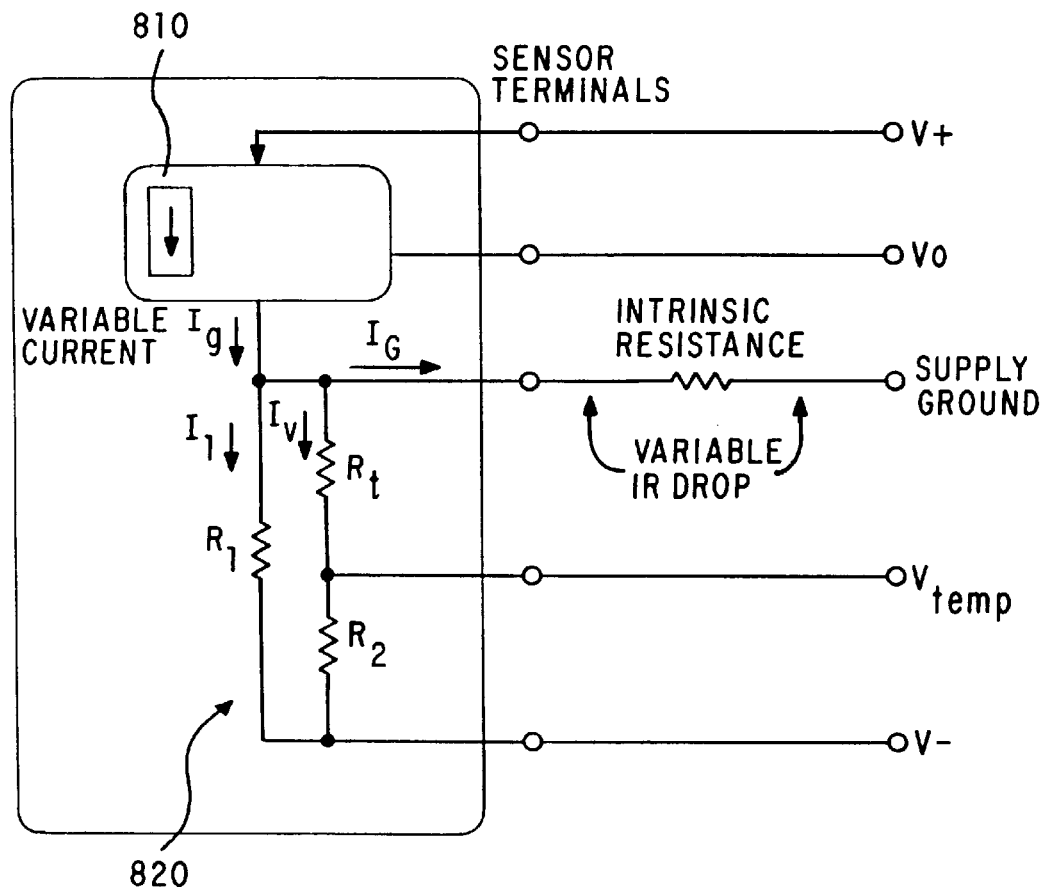
FIG. 8 is a schematic diagram of a pressure sensor with return current balancing circuitry.

FIG. 8 shows the schematic of how a temperature sensor is integrated with a pressure sensor. FIG. 8 is a diagram of an improved pressure sensor having a return current balancing circuit for passive current compensation. By introducing an additional voltage supply, V−, and a current balancing circuit comprising a temperature sensitive resistor, Rt, and two fixed resistors, R1 and R2 the return current to ground is greatly reduced. In particular, a current that varies with temperature is provided between the ground terminal and the negative supply, V−. The variable current is given by:

I1+IV=V−/R1+V−/(Rt+R2)

Since Rt is related to temperature, the variable current is a function of temperature. By suitably choosing Rt, R1 and R2, the variable current can be made substantially equal to the variable supply current, thereby greatly reducing the ground current. To ensure that the temperature of the pressure sensor is the same as the resistor Rt, the resistor can be enclosed in the same package with the sensor. As an additional benefit, the temperature sensitive resistor may be employed for providing an output voltage that varies with temperature. Properly calibrated, such an output voltage can be employed as a temperature sensor. In particular, the voltage output, Vtemp can be calculated as:

Vtemp=Rt/(Rt+R2)*V−

Since Rt is temperature dependent, Vtemp is directly related to temperature. This would provide good thermal matching between pressure and temperature sensing. By using a temperature sensitive resistor (Rt), the combination of R1 and R2 and Rt could provide both a temperature output Rt, R1 and R2 can be chosen such that the current supplied by the positive terminal, V+ of the pressure sensor is equal to the current that returns to the negative terminal of the pressure sensor, V−. This condition can be substantially held within the operating temperature of the pressure sensor, thus reducing the return current.

The key advantage is the simplicity of the design. By not heating the components, an increased operating temperature range is achieved. A lower operating, temperature than thermal zone improves reliability. There is no start-up time for the module since temperature of the module is kept at equilibrium at all time. There is also improved temperature performance since there is no temperature gradient due to the local heating of the heated component. The issues with the high start-up power, thermal control loop stability and line transient sensitivity do not exist.

Calibration reduces accuracy requirements on voltage references and analog components. This can be explained by assuming that an A/D is used as part of the data acquisition system, such that Vo of the sensors can be measured as a portion of the reference voltage. If both the A/D and the voltage reference are derived from the same source, the accuracy, temperature drift and low frequency noise of the reference source is not important. All temperature drift due to individual components on the module are lumped together as a single temperature drift term and calibrated out.

To achieve higher performance, current matching could reduce ground current over a wide temperature range by using temperature sensitive components to cancel ground current over a wide range of temperature. In our design, passive circuitry is used. It would allow the sensor to run at its full bandwidth without interaction with an active ground circuit which can cause stability and transient problem. Passive circuits are also less problematic with RF immunity and are more reliable. Several temperature sensors can be tied in parallel for any number of sensors in the configuration. Hence a single temperature reading can be used to reduce the number of A/D channels required.

While the invention has been described and illustrated with reference to specific embodiments in the area of gas chromatography, those skilled in the art will recognize that modification and variations may be made such that the invention is equally applicable to the field automotive engine design, or other fields where compensation for changes in ambient temperatures and pressures is required for measurement and control of fluid supplies. For example, the fuel/air mixture of an automotive engine is typically controlled by measuring air flow through an intake manifold and then controlling the amount of fuel injected into the intake manifold. The invention is very applicable to this application and may be employed to enhance engine operating efficiency and performance.

What is claimed is:

1. A return current balancing circuit for use with a pressure sensor having a return current which varies with temperature, the return current causing voltage fluctuations in a conductor that couples the pressure sensor to ground, comprising:

a first voltage supply terminal coupled to a first supply voltage (V+), a return current terminal coupled by the conductor to ground and providing a return path for the return current, a second voltage supply terminal coupled to a second supply voltage (V−), the second supply voltage having a lower potential than said ground, and a variable resistive circuit connected between said return current terminal and said second voltage supply terminal, the resistive circuit having a resistance which varies with temperature, whereby a variable current flowing through the resistive circuit substantially reduces the return current.

2. The return current balancing circuit as claimed in claim 1, wherein the return balancing circuit couples the pressure sensor to a data acquisition system having a ground reference, and wherein, the variable resistive circuit substantially reduces the return current from the pressure sensor to the ground reference of the data acquisition system and substantially reduces the voltage drop associated with the intrinsic resistance of the conductor coupling the sensor's ground terminal to the data acquisition system ground reference.

3. The return current balancing circuit as recited in claim 2, said variable resistive circuit further comprising:
- a first fixed resistor R1 connected between said return current terminal and said second voltage supply terminal;
- a second fixed resistor R2 connected at one end to said second voltage supply terminal; and
- a temperature sensitive resistor Rt connected between the other end of the second fixed resistor R2 and said return current terminal.

4. The return current balancing circuit as recited in claim 3, whereby the variable resistive circuit is incorporated as part of the sensor.

5. The return current balancing circuit as recited in claim 3, whereby the variable resistive circuit is incorporated as part of a module supporting multiple sensors.

6. The return current balancing circuit as recited in claim 3, said variable resistive circuit further comprising:
- a temperature measurement terminal Vtemp connected to the junction of said fixed resistor R2 and said temperature sensitive resistor Rt, wherein the voltage output (Vtemp=Rt/(Rt+R2)*V−), measured between said temperature measurement terminal Vtemp and said return current terminal is proportional to temperature.

* * * * *